United States Patent [19]

Gisby

[11] Patent Number: 5,658,887
[45] Date of Patent: Aug. 19, 1997

[54] PHARMACEUTICAL FORMULATIONS COMPRISING A CLAVULANIC ACID SALT AND ERITHROMYCIN DERIVATITE

[75] Inventor: Angela Suzanne Gisby, Horsham, England

[73] Assignee: SmithKline Beecham p.l.c.

[21] Appl. No.: 256,675

[22] PCT Filed: Jan. 22, 1993

[86] PCT No.: PCT/GB93/00150

§ 371 Date: Jul. 20, 1994

§ 102(e) Date: Jul. 20, 1994

[87] PCT Pub. No.: WO93/14770

PCT Pub. Date: Aug. 5, 1993

[30] Foreign Application Priority Data

Jan. 25, 1992 [GB] United Kingdom .................. 9201639

[51] Int. Cl.⁶ .................................................. A61K 31/70
[52] U.S. Cl. ................................................ 514/29; 514/81
[58] Field of Search ................................ 536/7.1; 514/29, 514/81

[56] References Cited

U.S. PATENT DOCUMENTS

| 4,299,826 | 11/1981 | Luedders | 514/29 |
| 4,935,247 | 6/1990 | Marttila et al. | 424/494 |
| 5,114,929 | 5/1992 | Vardan | 514/29 |

FOREIGN PATENT DOCUMENTS 2 005 538  4/1979  United Kingdom.

*Primary Examiner*—Elli Peselev
*Attorney, Agent, or Firm*—Wayne Dustman; Charles M. Kinzig; Edward T. Lentz

[57] ABSTRACT

A pharmaceutical formulation comprising a pharmaceutically acceptable salt of clavulanic acid in combination with erythromycin and another antimicrobial agent useful for the treatment of an infection by intracellular pathogens in humans or animals.

7 Claims, 6 Drawing Sheets

PHARMACEUTICAL FORMULATIONS COMPRISING A CLAVULANIC ACID SALT AND ERYTHROMYCIN DERIVATITE

This invention relates to pharmaceutical formulations, in particular to novel uses of formulations in connection with the treatment of infection by intracellular pathogens, in particular microorganisms of the genus Legionella, particularly *L. pneumophila*.

Intracellular pathogens include microorganisms of the genus Legionella, Chlamydia (e.g. *C. trachomatis* and *C. pneumoniae*) and Mycobacterium (e.g *M. avium, M. fortuitum* and *M. tuberculosis*). Legionella spp. are known to infect the respiratory tract of humans and animals, causing acute and sometimes fatal symptoms. It is known to treat Legionella infection with antibiotics, for example erythromycin. It is an object of this invention to provide alternative and improved pharmaceutical treatments for Legionella infection.

The invention provides a pharmaceutical formulation which comprises a pharmaceutically acceptable salt of clavulanic acid, in combination with erythromycin or a derivative thereof, and optionally one or more other antimicrobial agents.

The formulation of the invention is suitable for use in the treatment of infection by intracellular pathogens, e.g. microorganisms of the genus Legionella, in humans or animals.

The present invention also provides a method of use of a pharmaceutically acceptable salt of clavulanic acid and erythromycin or a derivative thereof, and optionally one or more other antimicrobial agents, together in combination in the manufacture of a medicament formulation, particularly a formulation for the treatment of infection of humans or animals by intracellular pathogens such as microorganisms of the genus Legionella.

The present invention further provides a method for the preparation of a pharmaceutical formulation as defined above, which method comprises admixing the combination of a pharmaceutically acceptable salt of clavulanic acid, and erythromycin or a derivative thereof and optionally one or more other antimicrobial agents.

As salts of clavulanic acid are extremely hygroscopic such formulations must be prepared in dry conditions, typically at a relative humidity of 30% or less. All constituents of the formulation should be predried.

The present invention further provides a pharmaceutical formulation as defined above for use as an active therapeutic substance, particularly in the treatment of infection of humans or animals by intracellular pathogens, such as microorganisms of the genus Legionella.

Further the invention provides a method for the treatment of an infection by intracellular pathogens, such as microorganisms of the genus Legionella in humans or animals, which comprises administering thereto, simultaneously or successively in any order, a pharmaceutically acceptable salt of clavulanic acid and erythromycin or a derivative thereof, and optionally one or more other antimicrobial agents. Typically the clavulanic acid and erythromycin may be co-administered together, e.g as a composition, optionally also together with one or more other antimicrobial agents.

Although this invention is not limited to any particular mode of operation, there appears to be an in-vivo synergistic interaction between the clavulanic acid and the erythromycin against Legionella, and the combination appears to be capable of penetrating mammalian cells.

Typical microorganisms of the genus Legionella are *L. pneumophila*. *L. micdadei* and *L. bozemanii* are also important pathogens.

The most pharmaceutically stable salt of clavulanic acid is the potassium salt, ie potassium clavulanate.

Suitable derivatives of erythromycin include the ethylsuccinate, acistrate, estolate, glucoheptonate, propionate, stearate and the lactobionate.

Suitable optional other antimicrobial agents which may be included in the formulations and methods of this invention as described herein include antibiotics, e.g β-lactam antibiotics such as penicillins and cephalosporins. Suitable antibiotics include those for example listed in GB 1578739, e.g on page 3 line 25 to 36 thereof. Preferred β-lactam antibiotics are amoxycillin and ticarcillin, especially amoxycillin, used as the free acid or as a pharmaceutically acceptable salt or ester. Amoxycillin may suitably be used as its trihydrate or sodium salt. Ticarcillin may suitably be used as its sodium salt.

The clavulanic acid and erythromycin and other optional antimicrobial agents, as used in this invention, whether in the form of the free acids, salts, esters or derivatives thereof are preferably each in a substantially pure form, e.g. at least 60% pure, more suitably at least 75% pure, preferably at least 85% especially at least 98% pure on a weight basis.

The formulations of the invention may be in a form adapted for oral or parenteral use and may be used for the treatment of infection in humans and animals especially mammals, including in particular domesticated animals (including farm animals).

The formulations of the invention may, for example, be made up in the form of tablets, suspensions, solutions, reconstitutable powders, and sterile forms suitable for injection or infusion. Such formulations may contain conventional pharmaceutically acceptable materials, for example solid or liquid diluents, colours and preservatives, in accordance with conventional pharmaceutical practice in a manner well understood by those skilled in the art of formulating antibiotics. Normally all such ingredients are predried. Aqueous solutions are normally provided in the form of dry ingredients for reconstitution immediately prior to use.

It can be particularly advantageous for the formulations of the invention to be administered to a patient by injection or infusion. That method of administration has the advantage of rapidly resulting in high blood levels of the active ingredient compounds being administered. Accordingly, in one preferred form of the formulation of the invention, the compounds are present in sterile form, including in sterile crystalline form. A further preferred form of the formulation of the invention, is one in which the formulation is in injectable or infusable form.

One injectable or infusable form of the formulation of the invention is an injectable or infusable solution, which suitably comprises an aqueous solution of a pharmaceutically acceptable salt of clavulanic acid and erythromycin or a derivative thereof, and optionally one or more other antimicrobial agents, in a sterile pyrogen-free liquid, for example water or aqueous ethanol. Because of the water sensitivity of salts of clavulanic acid such a formulation must be provided as the dry constituents and be made up with water immediately prior to use.

A further injectable or infusable form of the formulation of the invention is an injectable or infusable suspension, in which case the salt of clavulanic acid, and erythromycin or a derivative thereof are advantageously present in finely particulate form. The suspension may be an aqueous suspension in, for example, sterile water or sterile saline, which may additionally include a suspending agent, for example polyvinylpyrrolidone. Alternatively, the suspension may be an oily suspension in a pharmaceutically acceptable oil suspending agent, for example arachis oil, which should be dry. Because of the water sensitivity of clavulanic acid salts such aqueous suspensions must be made up from dry constituents immediately prior to use.

A formulation according to the invention may be in unit dosage form, for example unit dosage form for parenteral administration, which will primarily include administration by injection or infusion, especially intramuscular and intravenous administration.

In the formulations and methods according to the invention, the erythromycin or derivative thereof may be administered to the patient in an antibacterially effective amount, and the salt of clavulanic acid may be administered in an amount effective to inhibit β-lactamase enzymes.

The salt of clavulanic acid will generally be administered in an amount sufficient to inhibit the β-lactamase enzyme(s) associated with infecting bacterial organism(s). To that end, it may suitably be administered to the patient at a daily dosage of from 0.3 to 15 mg/kg, preferably from 0.7 to 10 mg/kg, for example from 0.7 to 7 mg/kg, of body weight. For an adult human (of approximately 70 kg body weight), from 25 to 1000 mg, preferably from 50 to 500 mg, of the salt of clavulanic acid be administered daily, suitably in from 1 to 6, preferably from 2 to 4, separate doses. Higher or lower dosages may, however, be used in accordance with clinical practice.

When the formulations according to the invention are presented in unit dosage form, each unit dose may suitably comprise from 12.5 to 1000 mg, preferably from 12.5 to 250 mg, of the salt of clavulanic acid. Each unit dose may, for example, be 12.5, 25, 50, 75, 100, 125, 150, 200, or 250 mg of the salt of clavulanic acid.

The ratio of the amount of the salt of clavulanic acid used according to the invention: amount of any other optional antimicrobial agent present may vary within a wide range, e.g 1:1 to 1:30 by weight. In the case of amoxycillin or salts or esters thereof the said ratio may, for example, be from 1:1 to 1:12; more particularly, it may, for example, be from 1:1 to 1:7, 1:1 to 1:4 or 1:1 to 1:2, by weight.

The amount of any optional other antimicrobial agent, e.g amoxycillin or salts or esters thereof in a formulation according to the invention will normally be approximately similar to the amount in which it is conventionally used per se In the case of amoxycillin for example from 125 to 3000 mg per day, and from 125 to 3000 mg per unit dose, advantageously from about 125 to 1000 mg per unit dose, from 2 to 4 times daily may be administered. In the case of ticarcillin for example a maximum of 3.2 g six to eight hourly may be administered.

The amount of erythromycin or derivative thereof in a formulation according to the invention will normally be approximately similar to the amount in which it is conventionally used per se, for example up to 4000 mg per day, typically for Legionella treatment 1000–4000 mg per day, for from 125–1000 mg per unit dose, administered from 2 to 4 times daily.

An example of a suitable formulation for oral administration according to the invention is one comprising from 12.5 to 250 mg, preferably from 25 to 125 mg, of potassium clavulanate, in admixture or conjunction with 250–4000 mg of erythromycin or a derivative thereof per unit dose, optionally also comprising 125 to 3000 mg of amoxycillin trihydrate.

An example of a suitable formulation for parenteral administration according to this invention is one comprising from 12.5 to 250 mg, preferably from 25 to 125 mg, of potassium clavulanate, in admixture or conjunction with 250–4000 mg of erythromycin or a derivative thereof per unit dose, optionally also comprising 125 to 3000 mg of sodium amoxycillin.

The following examples illustrate the synergistic antibacterial activity of a salt of clavulanic acid and erythromycin in combination and compare it with the activity of amoxycillin and a salt of clavulanic acid alone, and of erythromycin used alone against Legionella pneumophila.

EXAMPLE 1

Figure 1:
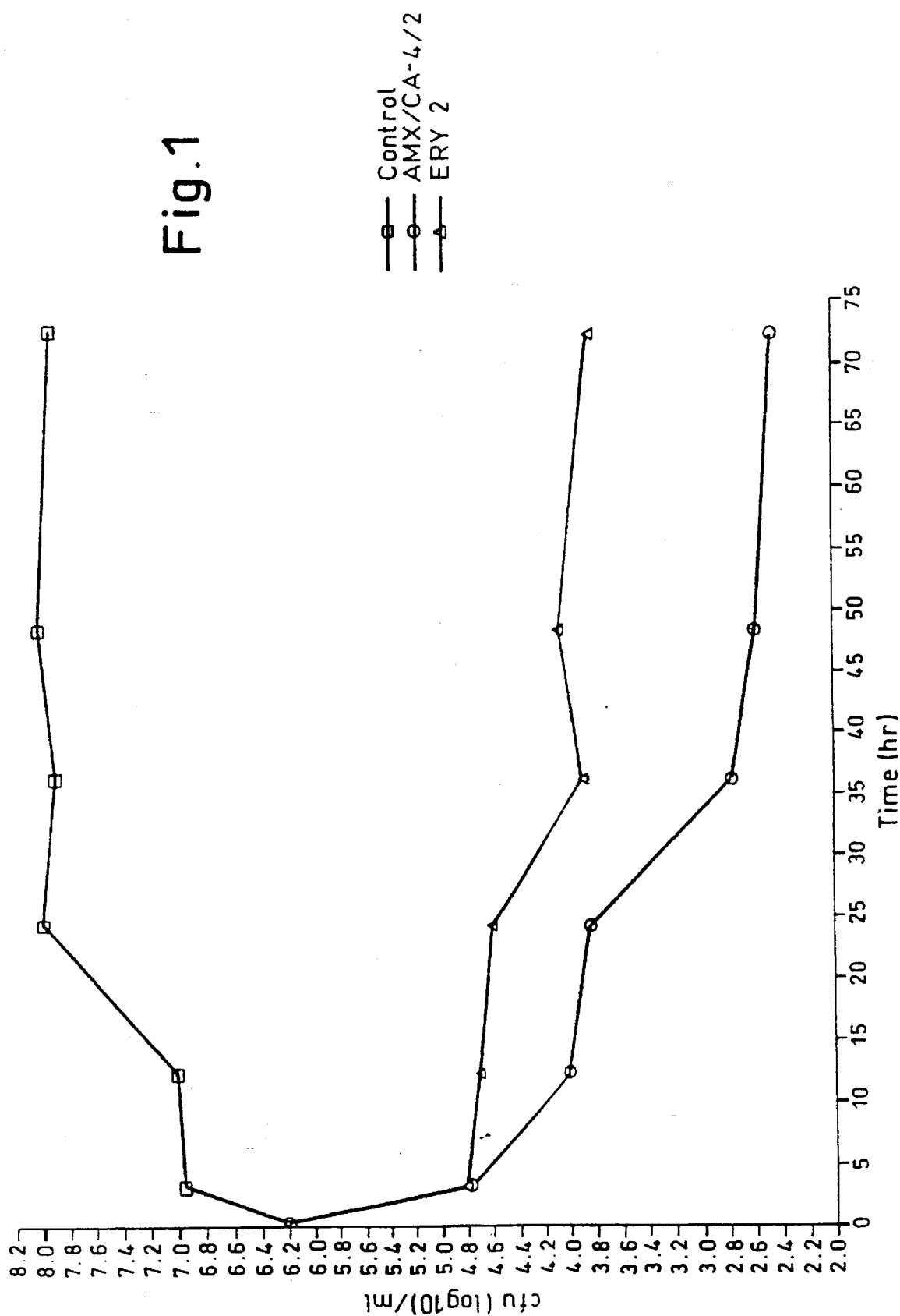
FIGS. 1 to 5 show graphically the level of L. pneumophila growth in vitro following administration of various formulations of the invention compared with comparisons and controls.
Figure 2:
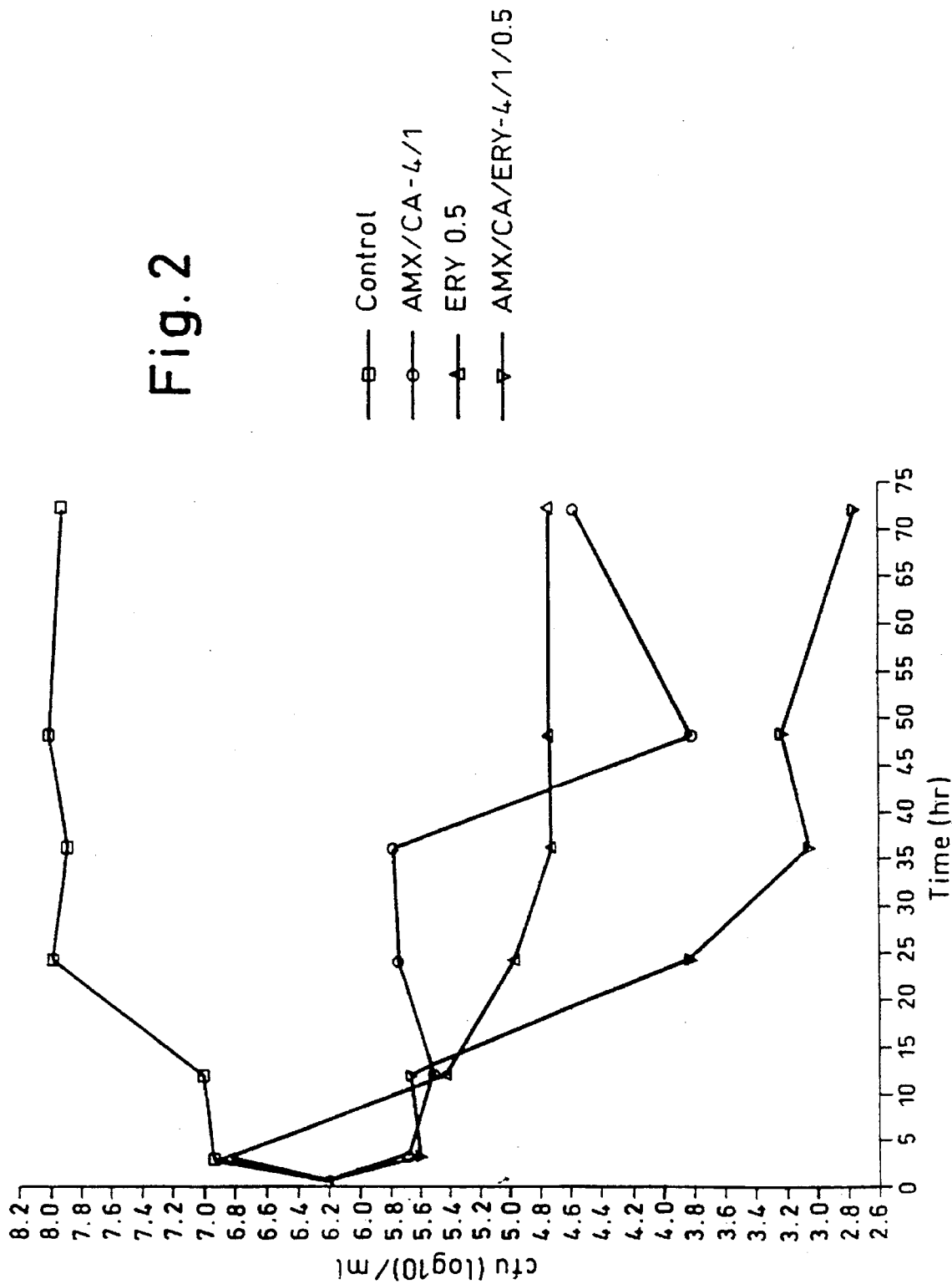
Figure 3:
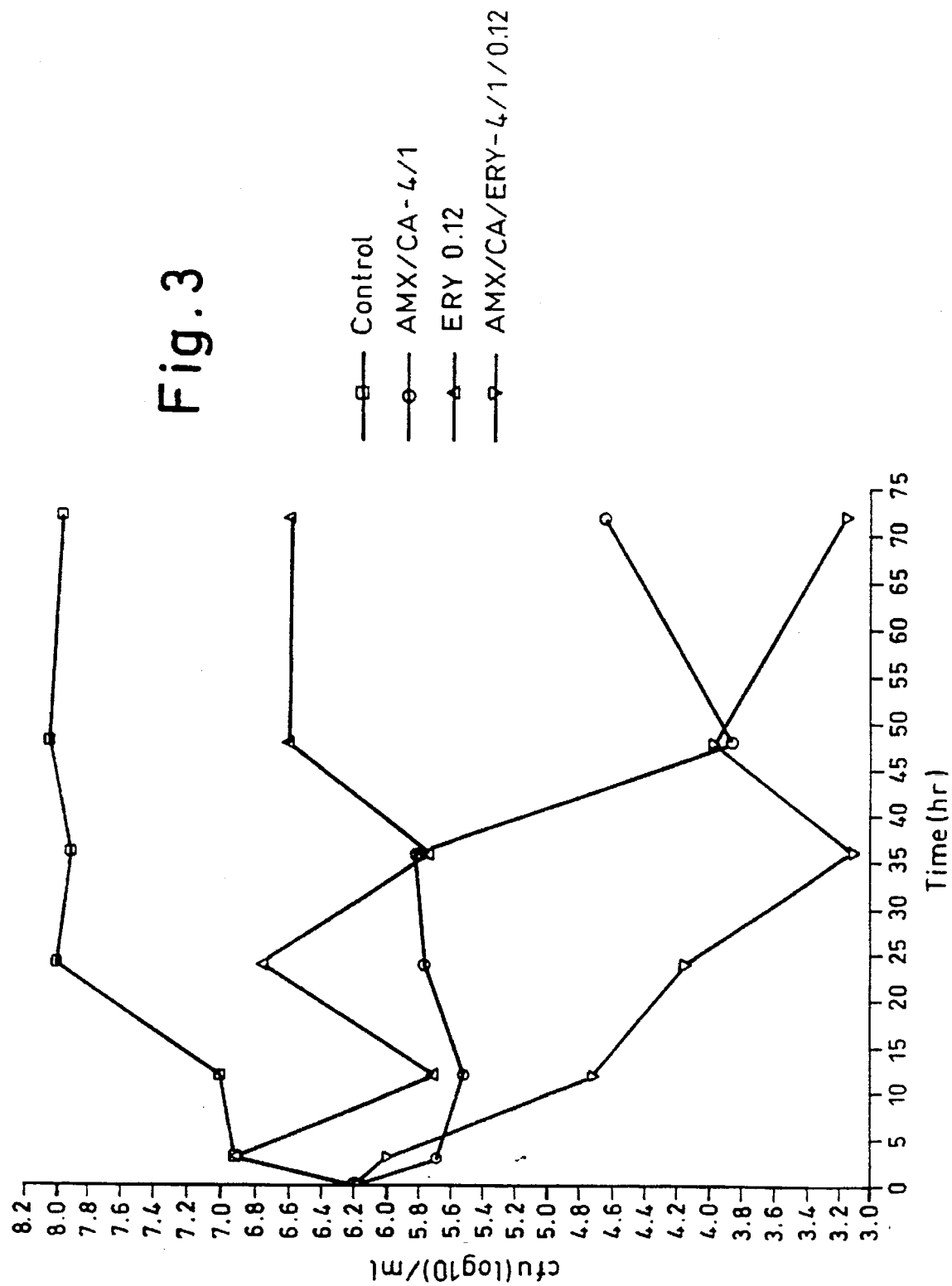
Figure 4:
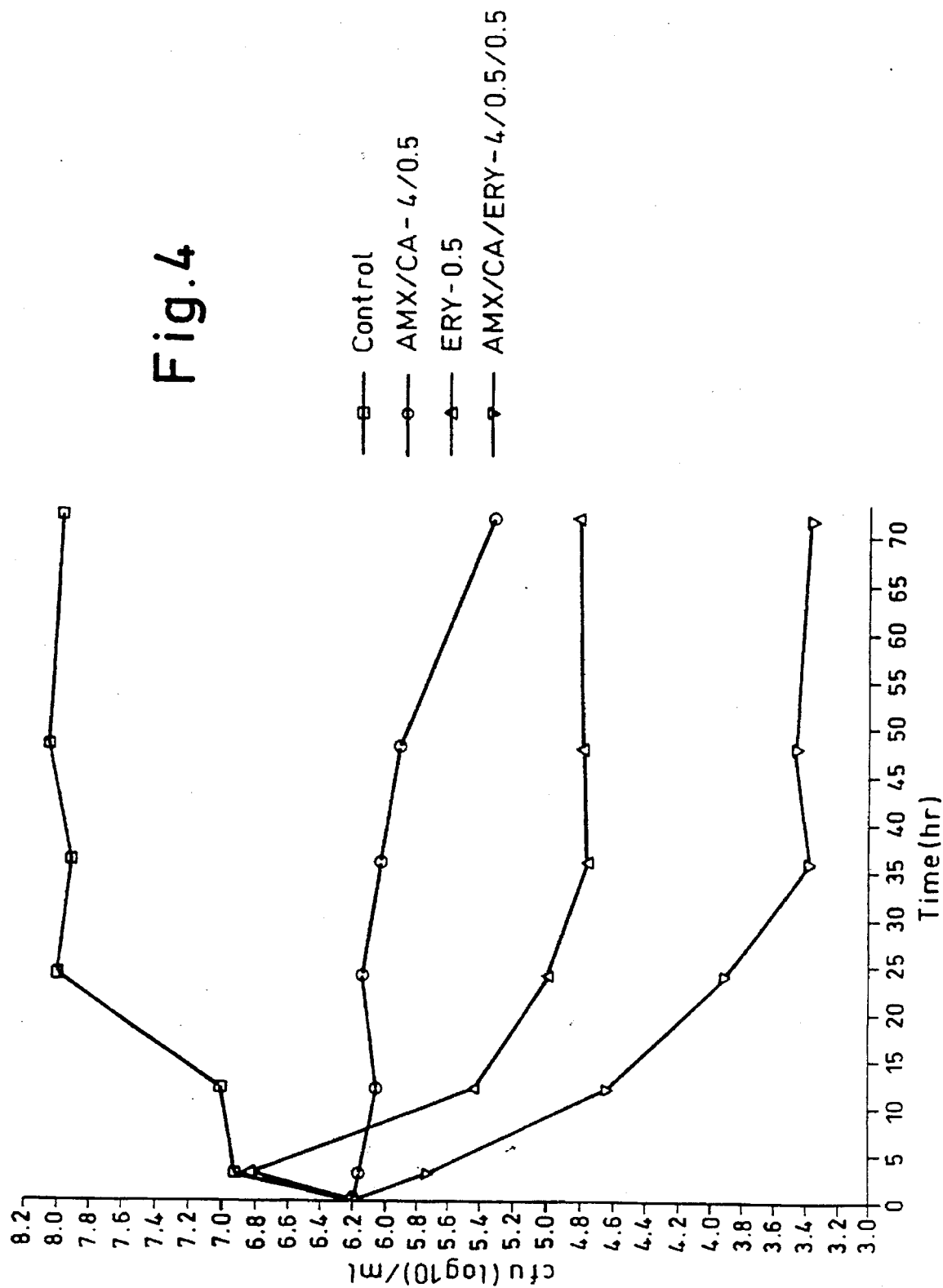
Figure 5:
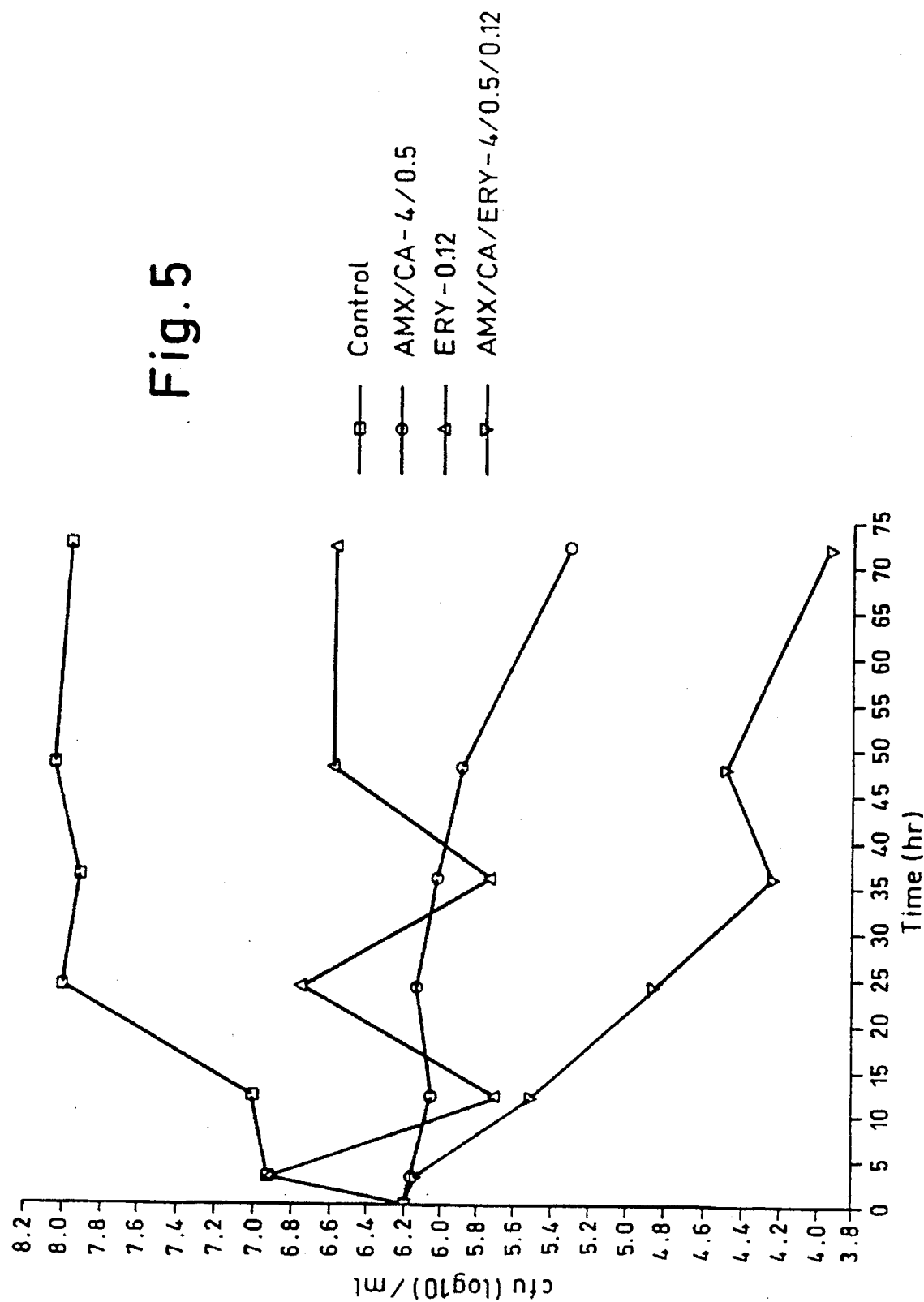

Methods:

Human foetal lung fibroblast (MRC-5) cells were growth to 80% confluency in 6-well plates, using tissue culture medium (TCM). TCM was Minimal Essential Medium with Earles' salts, supplemented with 10% foetal calf serum, 2 mM L-glutamine and 1% non-essential amino acids. The medium was removed and replaced with fresh TCM containing $1.0 \times 10^7$ cfu/ml L. pneumophila 1624. The plates were re-incubated for a further 16 h to allow the organisms to become intraceullar.

The inoculant was withdrawn and the infected cells washed to remove any adherent extracellular bacteria. Fresh TCM containing antibiotics, or drug-free TCM, was added. Doses were repeated in this way 12, 24 and 36 h later.

Amoxycillin trihydrate and lithium clavulanate* were laboratory reference preparations, and erythromycin lactobionate was a commercial preparation for injection (Erythrocin, Abbott). The concentrations tested were as follows (μg/ml): amoxycillin (AMX) 4; erythromycin (ERY) 2, 0.5, 0.12; amoxycillin/lithium clavulanate acid (AMX/CA) 4/2, 4/1, 4/0.5; AMX/CA+ERY 4/1+0.5, 4/1+0.12, 4/05+0.5, 4/0.5+0.12.

*Although laboratory standard lithium clavulanate is used in these examples it should be noted that because of the effects of small amounts of lithium in the treatment of brain disorders lithium clavulanate is not considered suitable for use in antibiotic therapy.

At intervals up to 72 h after addition of antibiotics, the infected cells were washed and lysed with distilled water. Vigorously triturated lysates were serially diluted in Mueller-Hinton broth and plated onto Buffered Charcoal Yeast Extract agar (with Legionella growth supplement) and onto 5% blood agar. Colony forming units were enumerated after 3 days' incubation.

Results AMX/CA (4/2) was more bactericidal than ERY (2), reducing the numbers of intracellular legionellae to $2.83\times10^2$ cfu/ml by 72 h, compared with $6.67\times10^3$ cfu/ml for ERY (FIG. 1). AMX/CA (4/1) and ERY (0.5) demonstrated equal activity but this was reduced in comparison with the higher concentrations (FIG. 2). At 4/0.5 μg/ml and 0.12 μg/ml respectively, AMX/CA and ERY were bacteristatic only, intracellular organisms remaining at the level of the starting inoculum for the duration of the test (FIG. 5). A synergistic effect was observed between AMX/CA and ERY in combination. AMX/CA (4/1)+ERY (0.5) or (0.12) reduced the numbers of *L. pneumophila* to $5.5\times10^2$ and $1.37\times10^3$ cfu/ml by 72 h (FIG. 2 & 3), and counts of $2.17\times10^3$ and $8.17\times10^3$ cfu/ml were recovered from cells exposed to AMX/CA (4/0.5)+ERY (0.5) or (0.12) (FIG. 4 & 5). Thus, concentrations of AMX/CA and ERY which were sub-effective alone were bactericidal in combination, showing activity similar to AMZX/CA (4/2) and ERY (2).

EXAMPLE 2

Materials and Methods 0p Animals: Weanling male rats (60–80 g, CD strain) were supplied by Charles River UK Ltd.

Induction of leukopenia: Rats were dosed intraperitoneally with 0.5 ml cyclophosphamide (Endoxana, Boehgringer Ingelheim Ltd, Bracknell). at 50 mg/kg three days before, and on the day of infection.

Organism: *L. pneumophila* 1624 (serogroup 1) was used.

Inoculum: *L. pneumophila* 1624 was grown on BCYEα agar for three days at 37° C. and the growth was suspended in Mueller Hinton (MH) broth (BBL). The suspension was standardized using a nephelometer to yield a count of 7–8 log 10 cfu/ml, and this was further diluted 1:1000 in MH broth.

Anaesthesia: Rats were anaesthetised by separate intramuscular injections of 50 µl of fentanyl fluanisone at 0.1 ml/kg(Hypnorm, Janssen Pharmaceuticals Ltd., Grove) and diazepam at 0.5 mg/kg(Valium, Roche products Ltd, Welwyn Garden City). The drugs were prepared in sterile distilled water.

Infection: Anaesthetised rats were infected by intrabronchial instillation of a 50 µl inoculum containing 4–5 log 10 cfu *L.pneumophila* by means of non-surgical intratracheal intubation.

Compounds: Amoxycillin trihydrate and potassium clavulanate (SmithKline Beecham Pharmaceuticals, Worthing) were dissolved in pH8.0 phosphate buffer and sterile distilled water respectively. Erythromycin base was dissolved in 10% ethanol and 1% hydroxypropylmethylcellulose (HPMC).

Dosage: Groups of 5 rats received 0.5ml of each agent by oral gavage. Therapy commenced 6 h post infection, and continued q.i.d. for four days (erythromycin t.i.d. because of its longer half life). Rats received amoxycillin alone at 200 mg/kg, amoxycillin/potassium clavulanate at 200/100 mg/kg, erythromycin at 100 mg/kg, or amoxycillin/potassium clavulanate acid+erythromycin at 200/100 mg/kg+100 mg/kg.

Results

Figure 6:
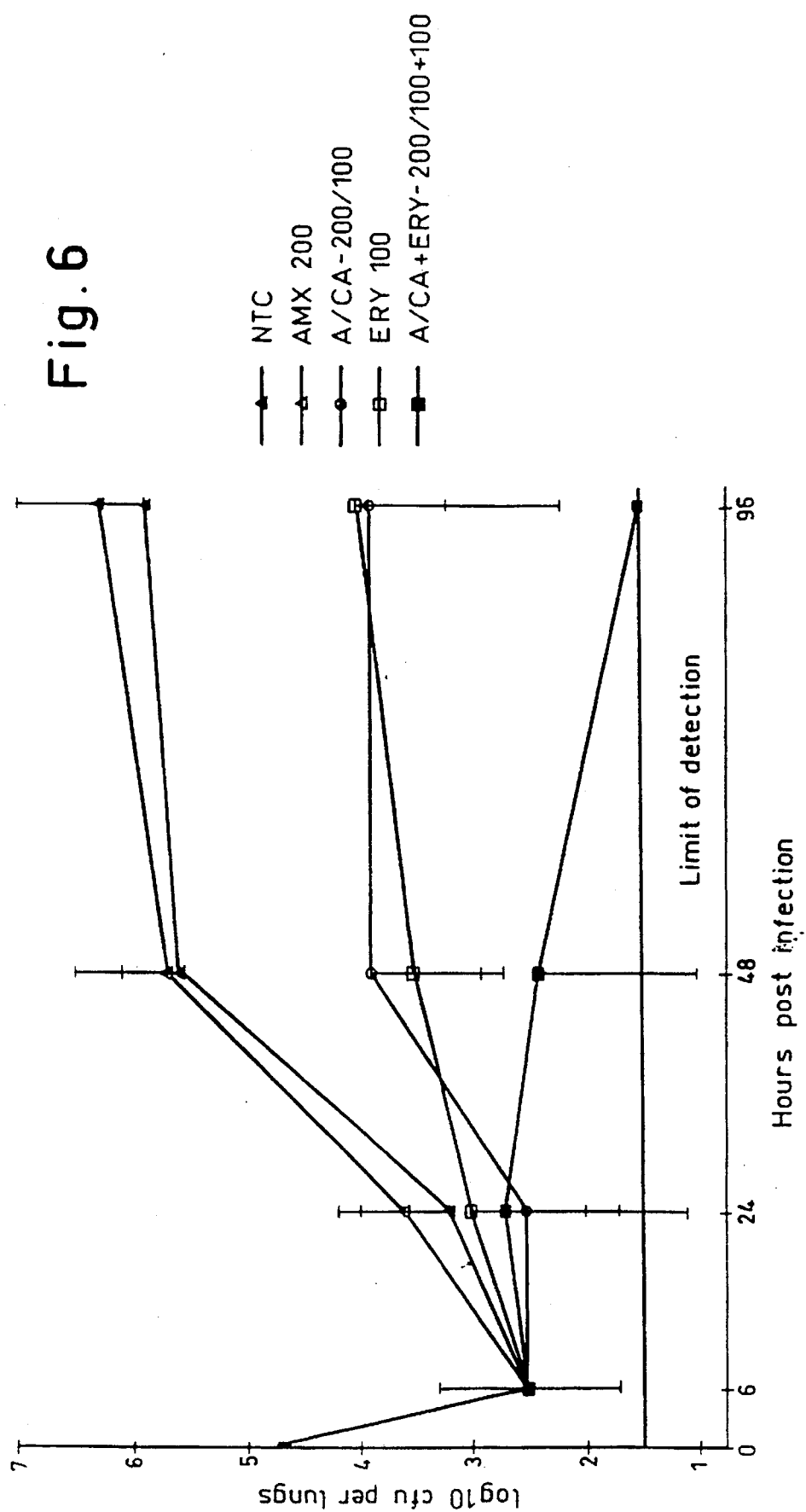
FIG. 6 shows graphically the level of L.pneumophila growth in vivo following administration of formulations of the invention compared with comparisons and controls.

The study shows a typical *L. pneumophila* pneumonia in rats (FIG. 6). The organism grew well in the rats' lungs, with 5.6±0.9 log 10 cfu/lungs detectable by 48 h, and 5.9±1.1 log10 cfu/lungspresent at 96 h post infection, although there were no mortalities. Amoxycillin at 200 mg/kg was ineffective, with numbers of legionellae recovered being similar to the non-treated control groups throughout the study. Amoxycillin/potassium clavulanate at 200/100 mg/kg and erythromycin at 100 mg/kg were equally effective in significantly reducing numbers of the organism ($p<0.05$), with 3.9+1.0 and 3.5±0.8 log 10 cfu/lungs respectively detectable at 48 h, and 3.9+0.7 and 4.0+1.8 log, 10 cfu/lungs at 96 h post infection. However, the combination of amoxycillin/potassium clavulanate with erythromycin (200/100 mg/kg+100 mg/kg) was significantly more effective than either agent alone ($p<0.05$), in reducing numbers of the organism to 2.4+1.4 log 10 cfu/lungs by 24 h, and eliminating the organism to below the limit of detection (1.2 log 10 cfu/lungs) by 48 h, with still nothing detectable at 96 h post infection.

I claim:

1. A pharmaceutical formulation comprising a pharmaceutically acceptable salt of clavulanic acid in an amount effective to inhibit β-lactamase enzymes, and an antibacterially effective amount of amoxycillin, present as the free acid, or as a pharmaceutically acceptable salt or ester thereof and in combination with a synergistically and an antibacterially effective amount of erythromycin or a derivative thereof selected from the group consisting of; the ethylsuccinate derivative, the acistrate derivative, the estolate derivative, the glucoheptonate derivative, the propionate derivative, the stearate derivative and the lactobionate derivative.

2. A method for the preparation of a pharmaceutical formulation as defined in claim 1 which method comprises admixing a pharmaceutically acceptable salt of clavulanic acid, erythromycin or a derivative thereof selected from the group consisting of; the ethylsuccinate derivative, the acistrate derivative, the estolate derivative, the glucoheptonate derivative, the propionate derivative, the stearate derivative and the lactobionate derivative; and amoxycillin.

3. A method for the treatment of an infection by a microorganism of the genus Legionella, Chlamydia or Mycobacterium in humans or animals, which comprises administering thereto, simultaneously or successively in any order, a pharmaceutically acceptable salt of clavulanic acid in an amount effective to inhibit β-lactamase enzymes, and an antibacterially effective amount of erythromycin or a derivative thereof selected from the group consisting of; the ethylsuccinate derivative, the acistrate derivative, the estolate derivative, the glucoheptonate derivative, the propionate derivative, the stearate derivative and the lactobionate derivative; and an antibacterially effective amount of an antimicrobial agent amoxycillin, present as the free acid, or as a pharmaceutically acceptable salt or ester thereof, provided that the three compounds are present at the same time in the body in synergistic amounts.

4. A composition according to claim 1 wherein the pharmaceutically acceptable salt of clavulanic acid is potassium clavulanate.

5. A composition according to claim 1 wherein the ratio pharmaceutically acceptable salt of clavalanic acid: amoxycillin is in the range 1:1 to 1:30.

6. A composition according to claim 1 in unit dosage form comprising 12.5 to 1000 mg of a pharmaceutically acceptable salt of clavulanic acid and 125 to 1000 mg of ertyromycin or a derivative thereof.

7. A composition according to claim 6 comprising 125 to 3000 mg of amoxycillin or a derivative thereof.

* * * * *